(12) United States Patent
Choi et al.

(10) Patent No.: US 12,325,850 B2
(45) Date of Patent: Jun. 10, 2025

(54) MICROROBOT-BASED BIOMIMETIC SYSTEM

(71) Applicant: Daegu Gyeongbuk Institute of Science and Technology, Daegu (KR)

(72) Inventors: Hong Soo Choi, Daegu (KR); Jin Young Kim, Gyeonggi-do (KR); Seung Min Lee, Gyeongsangbuk-do (KR); Sang Won Kim, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 1302 days.

(21) Appl. No.: 16/312,757

(22) PCT Filed: Jun. 22, 2017

(86) PCT No.: PCT/KR2017/006590
§ 371 (c)(1),
(2) Date: Dec. 21, 2018

(87) PCT Pub. No.: WO2017/222321
PCT Pub. Date: Dec. 28, 2017

(65) Prior Publication Data
US 2019/0359928 A1 Nov. 28, 2019

(30) Foreign Application Priority Data

Jun. 22, 2016 (KR) .................. 10-2016-0077807
Jun. 22, 2016 (KR) .................. 10-2016-0077809
Jun. 22, 2016 (KR) .................. 10-2016-0077813

(51) Int. Cl.
*B01L 3/00* (2006.01)
*A61B 1/04* (2006.01)
(Continued)

(52) U.S. Cl.
CPC ............... *C12M 35/08* (2013.01); *A61B 1/04* (2013.01); *B01L 3/50273* (2013.01);
(Continued)

(58) Field of Classification Search
CPC ...... C12M 29/00; C12M 21/08; C12M 23/16; C12M 41/00; C12M 35/08; C12M 35/06;
(Continued)

(56) References Cited

U.S. PATENT DOCUMENTS 8,382,896 B2 * 2/2013 Hansen ................... B01L 9/527
117/68
2006/0073540 A1 * 4/2006 Martel ..................... B82Y 5/00
435/34

(Continued)

FOREIGN PATENT DOCUMENTS

JP 2006-043607 A 2/2006
JP 2010-172112 A 8/2010
(Continued)

OTHER PUBLICATIONS

Lee et al., "Fabrication and Targeted Particle Delivery using microrobots", Oct. 28-30, 524-525. (Year: 2015).*
(Continued)

*Primary Examiner* — Liban M Hassan
(74) *Attorney, Agent, or Firm* — Sughrue Mion, PLLC

(57) ABSTRACT

The present invention relates to a microrobot-based biomimetic system for delivering a drug or cell, organizing microorgans, and controlling fluid flow. The microrobot-based biomimetic system according to one aspect of the present invention comprises: a network for interconnecting microorgans constituting a biometric organ model; a microrobot for delivering a targeted drug or cell while moving in the network; and a magnetic field control unit for controlling an operation of the microrobot.

6 Claims, 5 Drawing Sheets

(51) Int. Cl.
- *C12M 1/00* (2006.01)
- *C12M 1/34* (2006.01)
- *C12M 1/42* (2006.01)
- *C12M 3/00* (2006.01)
- *C12M 3/06* (2006.01)

(52) U.S. Cl.
CPC ............ *C12M 21/08* (2013.01); *C12M 23/16* (2013.01); *C12M 29/00* (2013.01); *C12M 41/00* (2013.01); *B01L 2200/143* (2013.01); *B01L 2300/12* (2013.01); *B01L 2300/16* (2013.01); *B01L 2400/043* (2013.01)

(58) Field of Classification Search
CPC ........... B01L 3/50273; B01L 2200/143; B01L 2300/12; B01L 2300/16; B01L 2400/043; G01N 35/00; G01N 35/08; A61B 34/30; A61B 34/00; A61B 1/04
USPC ...................................................... 435/286.2
See application file for complete search history.

(56) References Cited

U.S. PATENT DOCUMENTS

| | | | | |
|---|---|---|---|---|
| 2012/0135452 | A1* | 5/2012 | Shuler | C12M 21/08 435/29 |
| 2014/0045179 | A1* | 2/2014 | Wang | B01J 20/32 435/6.11 |
| 2014/0225694 | A1* | 8/2014 | Sitti | F04D 29/426 335/295 |
| 2014/0302110 | A1* | 10/2014 | Choi | A61K 41/00 424/423 |
| 2015/0351856 | A1 | 12/2015 | Choi et al. | |

FOREIGN PATENT DOCUMENTS

| | | | |
|---|---|---|---|
| KR | 10-2015-0142150 A | 12/2015 | |
| WO | WO-03027223 A2 * | 4/2003 | ............ C12M 23/16 |

OTHER PUBLICATIONS

Chowdhury et al., "Controlling multiple microrobots: recent progress and further challenges", J Micro-Bio Robot 10:1-11 (Year: 2015).*

Sangwon Kim et al., "Fabrication and Characterization of Magnetic Microrobots for Three-Dimensional Cell Culture and Targeted Transportation", Advanced Materials, 2013, pp. 5863-5868, vol. 25.

Jae Won LEE, "New Drug Experiment by using Human on a Chip . . . Good job, mouse", Article of ChosunBiz, May 31, 2011, 2 pgs.

Se Mi Jeong et al., "(A) Study on Electromagnetic Actuated Microrobot System for Locomotion and Treatment in Blood Vessel using Gradient and Precessional Magnetic Fields", doctor's thesis, Chonnam National University Graduate School, Feb. 2013, pp. 1-118 Feb. 2013, pp. 1-118.

International Search Report for PCT/KR2017/006590 dated Sep. 20, 2017 (PCT/ISA/210).

* cited by examiner (a)

(b)

MICROROBOT-BASED BIOMIMETIC SYSTEM

CROSS REFERENCE TO RELATED APPLICATIONS

This application is a National Stage of International Application No. PCT/KR2017/006590 filed Jun. 22, 2017, claiming priority based on Korean Patent Application No. 10-2016-0077807, filed Jun. 22, 2016, Korean Patent Application No. 10-2016-0077809, filed Jun. 22, 2016, and Korean Patent Application No. 10-2016-0077813, filed Jun. 22, 2016.

TECHNICAL FIELD

The present invention relates to a microrobot-based biomimetic system configured to perform drug or cell delivery, construction of a microorgan, and control of a fluid flow.

BACKGROUND ART

Techniques related to testing in a human body simulation system have been proposed to improve predictability of a result of a clinical trial using a new drug candidate material, to maximize the development efficiency of a new drug material, and to solve ethical problems related to animal experimentation.

It is impossible to apply target-directed therapy directly to a clinical trial using a magnetic material (including a microrobot). Further, when an animal experiment with a target-directed therapeutic agent is performed immediately, reproducibility is low and clinical effects cannot be accurately predicted because an animal is used.

A technology using a human-on-a-chip or body-on-a-chip is proposed to solve the ethical problems related to animal experiments and to improve the accuracy of prediction of clinical effects, but there is no in vitro testing platform to test microrobot-based target-directed therapy in a physiological environment similar to the body before a clinical trial or an animal experiment.

The proposed technology is capable of precisely predicting in vivo physiological responses to chemicals and medicines by implementing an in vitro system as close to an actual human body as possible on a small chip by applying cell culture and microfluidic technologies. The proposed technology is evaluated as a substitute for animal experiments.

According to the conventional art, the first problem in the art of human-on-a-chip manufacturing is that there is a limit in implementing a system in terms of processes because a loading port and a channel should be provided. The second problem is that it is difficult to secure biometrics reliability for a bio-environment which constantly varies.

Regarding the first problem described above, according to the conventional art, a loading port and a channel need to be implemented in addition to an inlet and an outlet for fluid flow in order to guide a micro-tissue to an artificial organ chamber. However, the process of the implementation is complicated, and it is difficult to precisely control the position of an artificial microorgan.

Regarding the second problem described above, according to the conventional art, an external pump is applied to the human-on-a-chip to implement various environments such as change of a fluid speed in the system. However, the external pump allows a fluid to flow only in one direction with respect to the whole system, and thus it is difficult to implement a biometric environment. Further, when the external pump is applied, it is difficult to dock a microorgan on a specific target portion. In order to overcome the above-described problems, installing valves controlled by air pressure and physical pressure in the system has been proposed. However, this method increases complexity of the system structure and fails to secure biometric reproducibility.

DISCLOSURE

Technical Problem

The present invention is directed to providing a microrobot-based target-directed in vitro testing platform for a therapeutic agent that is capable of testing, before a clinical trial, target-directed therapy using micro-/nano-robots (magnetic therapeutic agent carriers for target-directed therapy including micro-/nano particles).

That is, the present invention is directed to providing a microrobot-based biomimetic system that is implemented for development of in vivo target-directed therapy using a cell or a drug by integrating microrobots driven and controlled by a magnetic field into the biomimetic system and is thus capable of testing an effect according to delivery of a drug or cell to a target disease portion and testing the overall effect of a therapeutic agent on tissues/organs other than the target disease portion by driving a target-directed therapeutic agent carrier in a blood flow.

The present invention is also directed to providing a microrobot-based biomimetic system that is capable of precise and selective control of the position of an artificial microorgan and selective and adaptive fluid control over a network in response to change in a bio-environment due to cell or drug use in order to realize a dynamic environment related to interaction among specific body organs and the like.

Technical Solution

One aspect of the present invention provides a microrobot-based biometric system including a network connecting microorgans constituting a biological organ model, a microrobot configured to move within the network to perform target-directed delivery of a drug or cell, and a magnetic field controller configured to control operation of the microrobot.

ADVANTAGEOUS EFFECTS

A microrobot-based biometric system according to an exemplary embodiment of the present invention can deliver a drug or cell to an in vivo local portion in a network of various body organ models interconnected in the biometric system, thereby monitoring physiological responses to and effects of a new drug.

According to the present invention, microrobots are moved by a magnetic field applied from the outside. Accordingly, it is unnecessary to provide an additional inlet and channel for guiding a micro-tissue into an artificial organ chamber, and the positions of the microrobots constituting various artificial organs including three-dimensional cultured cells can be precisely controlled to accurately load the microrobots at a target position.

According to the present invention, by changing the rotation speed and rotation direction of a microrobot pump by using the microrobot pump driven by a magnetic field, change of the flow speed and the direction in the network can be selectively controlled. Thereby, a fluid can be controlled selectively as desired even without provision of an external pump or valve. Accordingly, it is possible to simulate a fluid flow (i.e., blood flow) so as to fit the characteristics and change in physiological state of a microorgan.

According to the present invention, control of the movement of the microrobot in the network and the fine movement in a corresponding microorgan chamber can be facilitated by forming a magnetic field in the entire area or local area of the biometric system using a magnetic field controller.

The effects of the present invention are not limited to those mentioned above, and other effects not mentioned will be clearly understood by those skilled in the art from the following description.

MODES OF INVENTION

The above and other objects, advantages, and features of the invention and methods of achieving them will be more clearly understood from the following detailed description of embodiments taken in conjunction with the accompanying drawings.

The present invention can be embodied in many different forms and should not be construed as being limited to the exemplary embodiments set forth herein. It is to be understood that the embodiments disclosed below are provided so that those skilled in the art can easily understand the objects, configurations, and effects of the present invention, and the scope of the present invention is defined by the claims.

It is to be understood that the terminology used herein is for the purpose of describing the exemplary embodiments only and is not intended to be limiting of the invention. In this specification, singular forms include plural forms unless the context clearly dictates otherwise. As used herein, the terms "comprises" and/or "comprising" are intended to indicate presence of stated components, steps, operations, and/or elements and do not exclude presence or addition of one or more other components, steps, operations, and/or elements.

Figure 1:
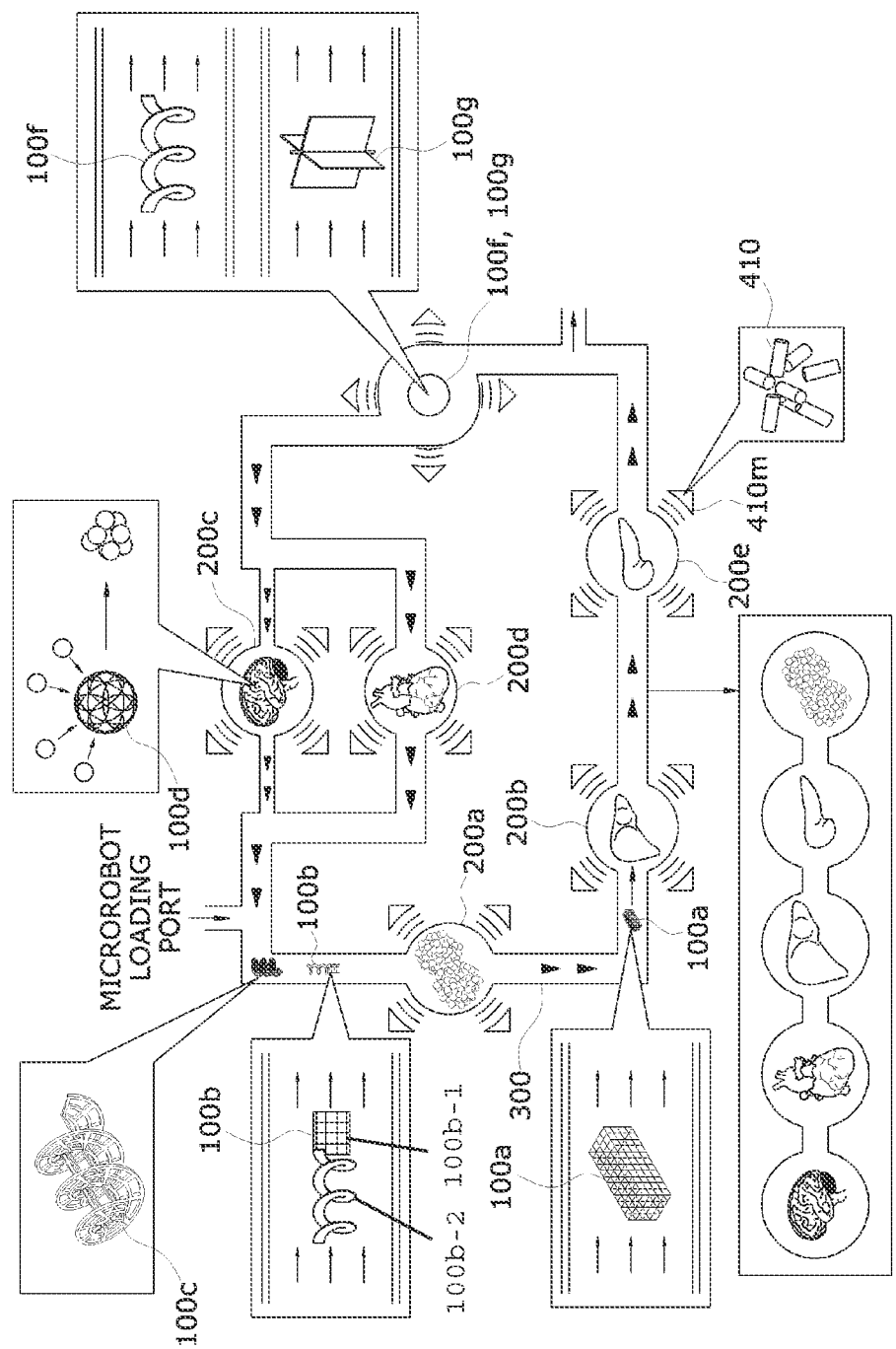
FIG. 1 is a configuration diagram illustrating a microrobot-based biometric system according to one exemplary embodiment of the present invention.
Figure 2:
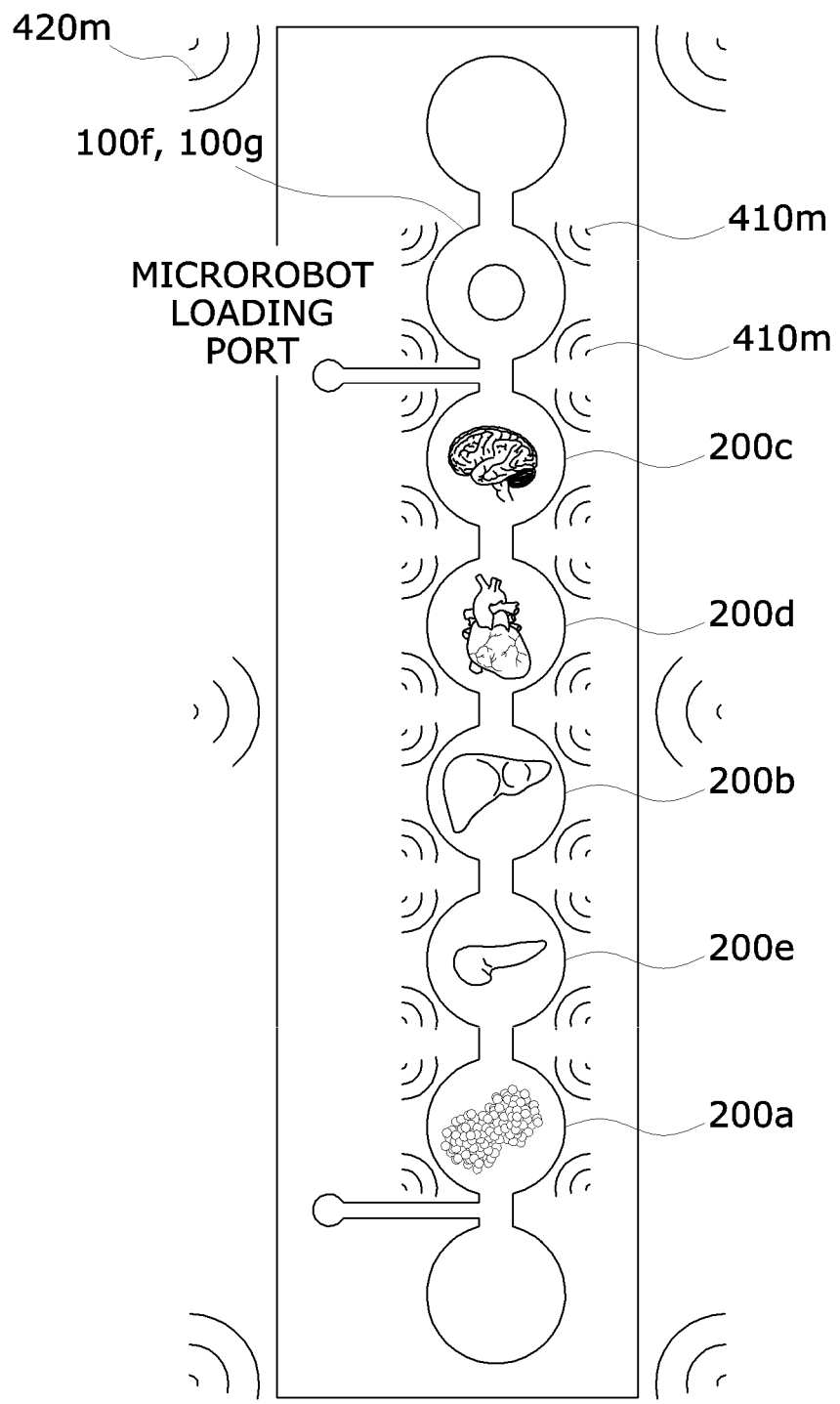
FIG. 2 is a view illustrating a global magnetic field control and a local magnetic field control according to one exemplary embodiment of the present invention.

FIGS. 1 and 2 illustrate a microrobot-based biometric system according to one exemplary embodiment of the present invention.

The microrobot-based biometric system according to one exemplary embodiment of the present invention includes a network 300 configured to connect microorgans 200 constituting a biological organ model, microbots 100a, 100b, and 100c introduced into the network 300 and transported by a magnetic field to perform target-directed drug or cell delivery, and a magnetic field controller configured to control operation of the microrobots.

The microorgans include a tumor, wherein 200a denotes a tumor, 200b denotes a liver, 200c denotes a brain, 200d denotes a cardiac organ, and 200e denotes a pancreas.

In the biomimetic system, the network 300 is a channel for biological interaction between the respective microorgans 200a to 200e.

For example, when a drug developed for the liver 200b, which is a microorgan, is administered, a biological interaction about how the drug administration affects the cardiac organ 200d, which is another microorgan, can take place.

The microrobots for cell or drug delivery may be of a bio-scaffold type, a capsule type, or a helical-scaffold type. These types are exemplary types described to facilitate understanding of the invention by those skilled in the art, and the shape of the microrobots of the present invention is not limited to the exemplary types.

In the embodiment of the present invention, in order to facilitate understanding of the invention by those skilled in the art, it is described as an example as shown in FIG. 1 that the microrobots 100a and 100b for cell or drug delivery include a bio-scaffold type microrobot 100a and a capsule type microrobot 100b. The microrobots may include a helical-scaffold type microrobot 100c to perform a corkscrew motion to secure a larger propulsion force.

The microrobots 100a, 100b, and 100c, which are of the bio-scaffold type or the capsule type, are accurately moved to a target microorgan in the network 300 by a magnetic field applied from the outside with a drug or cell loaded and then release the drug or cell.

When the microrobot is the bio-scaffold type microrobot 100a, the microrobot is provided therein with scaffolds arranged spaced apart from each other to form a plurality of gaps. Through these gaps, the cells are cultured three-dimensionally or stored in the internal space.

The bio-scaffold type microrobot 100a is a porous bio-scaffold of a three-dimensional structure and can be configured in a hexahedral, cylindrical, elliptical, polygonal, or conical shape. The bio-scaffold type microrobot is not limited to the above-described shapes but may be configured in various other shapes.

For example, the bio-scaffold type microrobot 100a is manufactured in lithography using a photocurable polymer and is thus formed as a porous bio-scaffold type microrobot of a micro-sized three-dimensional structure, which facilitates cell or drug delivery in the network 300 of the biometric system.

The bio-scaffold type microrobot 100a, which is a porous scaffold, loads a three-dimensional cultured cell or a drug into the internal space of the scaffold having gaps and moves in the network 300.

As shown in FIG. 1, the capsule type microrobot 100b includes a cap 100b-1 for loading a drug or a cell and a plunger 100b-2 connected to the cap 100b-1 and rotated by a magnetic 10 field and is thus capable of transporting and releasing the loaded cell and drug in the direction of a rotating magnetic field. In order to prevent any loss that may be incurred during movement, the cap may be sealed.

After the microrobot 100 is moved to the target microorgan, release of the cell and the drug is performed by a magnetic field that is applied by the magnetic field controller (wherein a local magnetic field controller is denoted by reference numeral 410 and a global magnetic field controller is denoted by reference numeral 420). While the bio-scaffold type microrobot and the capsule type microrobot are taken as an example of the shapes of the microrobots in order to facilitate understanding of the embodiment of the present invention, the method of delivery or release of the cell and the drug is not limited by the shapes of the microrobots or a specific technique.

For example, the microrobots 100a, 100b, and 100c configured to perform cell or drug delivery according to the embodiment of the present invention may be formed of a non-biodegradable material. In this case, after the scaffold is formed, the surface of the scaffold is coated with nickel or the like to impart magnetism thereto and is coated with titanium or the like for biocompatibility.

As another example, the microrobots 100a, 100b, and 100c configured to perform cell or drug delivery may be formed of a biodegradable material. In this case, coating the surfaces of the microrobots is avoided to ensure smooth in vivo bio-degradation. Instead, the scaffold is constructed with a mixture of iron oxide nanoparticles, which are a biocompatible magnetic material, and another bio-degradable material.

The above-described magnetic materials exhibit a certain intensity of magnetism and are composed of metals which have low corrosiveness. For example, iron, cobalt or neodymium may be used alone or in combination in addition to the above-described magnetic materials, and the entirety or a part of the outer circumferential surfaces of the microrobots 100a, 100b, and 100c configured to perform cell or drug delivery may be coated therewith.

The microrobots 100a, 100b, and 100c configured to perform cell or drug delivery according to the embodiment of the present invention can be coated with a protective layer formed of a biocompatible material. For example, the biocompatible material, titanium, medical stainless steel, alumina, or gold may be used alone or in combination.

In addition, the microrobots 100a, 100b, and 100c configured to perform cell or drug delivery according to the embodiment of the present invention may deliver a therapeutic agent for hyperthermia. The scaffold of the microrobot includes iron oxide magnetic nanoparticles. Thus, the scaffold is caused to generate heat by a magnetic field externally applied thereto and is triggered by heat generation to deliver a therapeutic drug.

That is, the iron oxide magnetic nanoparticles generate heat as the internal magnetic moment is aligned in the direction of the applied magnetic field. The scaffold is melted at a preset temperature by generated heat to trigger the therapeutic drug delivery.

According to the embodiment, the microrobot is caused to transport the loaded drug, therapeutic agent, or the like to a target by the magnetic field applied thereto. The scaffold of the microrobot is melted by a heat generation mechanism according to application of a specific magnetic field and frequency, and thus the loaded drug or therapeutic agent is released therefrom.

As shown in FIG. 1, regarding the brain 200c, a spherical microrobot 100d includes spherical scaffolds. The spherical microrobot 100d has a cell provided in a gap formed between the scaffolds and thus three-dimensionally cultures the cell. A part or the entirety of the spherical scaffolds of the spherical microrobot 100d is coated with a magnetic layer and is thus rolled by an external rotating magnetic field and loaded at a preset target position so as to form, for example, the microorgan 200c corresponding to the brain. The spherical scaffold structure of the spherical microrobot 100d contributes to formation of neurites, particularly, in the case of a brain model.

According to the present invention, by implementing artificial microorgans using microrobots in implementing the biometric system on a chip, the microrobots can be precisely arranged at a target position by a magnetic field applied from the outside through the magnetic field controller.

Therefore, even when a separate inlet and channel for guiding a micro-tissue to the artificial organ chamber are not realized for fabrication of the biomimetic system chip, the microorgan 200b can be accurately loaded individually at a preset position through a rolling movement, and multiple microorgans can be loaded together by rotating the microrobot 100d through interaction between the magnetism of the microrobot 100d and the rotating magnetic field of the microrobot 100d.

Hereinafter, driving of microrobot pumps 100f and 100g of the present invention will be described with reference to FIG. 1.

According to one exemplary embodiment of the present invention, the microrobot pumps 100f and 100g are arranged in a network 300 which connects the microorgans 200 constituting a biological organ model and are driven by an applied magnetic field to control fluid flow in the network 300.

As shown in FIG. 1, the microrobot pumps 100f and 100g include a screw-type microrobot pump 100f or a windmill-type microrobot pump 100g as typical types of microrobot pumps.

The blade of the windmill-type microrobot pump illustrated in the embodiment of the present invention may have a different shape such as a rectangular shape or a propeller shape. The microrobot pumps 100f and 100g are formed of or coated with a magnetic material ($Fe_2O_3$, $Fe_3O_4$, etc.). The magnetic material is a metal that has a certain intensity of magnetism and low corrosiveness.

For example, in addition to the above-described magnetic material, nickel, iron oxide, cobalt, neodymium, or the like may be used alone or in combination, and the outer surfaces of the microrobot pumps 100f and 100g may be fully or partially coated therewith.

In addition, the outer surfaces of the microrobot pumps 100f and 100g may be coated with a protective layer which is a biocompatible material.

Such biocompatible material may be, for example, titanium, medical stainless steel, alumina, gold, or a mixture thereof.

The microrobot pumps 100f and 100g according to the present invention are driven by the magnetism of the magnetic material thereof and a magnetic field applied thereto. The rotation speed or the rotation direction of the microrobot pumps 100f and 100g is changed according to the intensity or direction of the magnetic field, thereby changing the speed or direction of a fluid in the network 300.

The microrobot pumps 100f and 100g may be fixed to a wall surface of a microchannel constituting the network 300.

The length, height, angle, and degree of magnetization of the thread or blade of the screw-type microrobot pump 100f and the windmill-type microrobot pump 100g are determined according to a preset structure and a material specification, and the speed and direction of the fluid flow is selectively controlled by a local magnetic field applied to the microrobot pumps 100f and 100g.

While the microrobot pumps 100f and 100g are illustrated in FIGS. 1 and 2 as being arranged at a position adjacent to the brain 200c, the cardiac organ 200d, and the pancreas

200e, the microrobot pumps 100f and 100g can be arranged over the entire area of the network 300 as needed to simulate the blood flow.

Thereby, various fluid flows and physiological actions within the network 300 of the biomimetic system, i.e., the microchannel, can be simulated, even without an external pump or valve having a complex configuration.

For example, in the portion corresponding to the brain microorgan 200c where the speed of fluid movement is significantly low, the rotation speed of the microrobot pumps 100f and 100g is controlled to be low so as to maintain a low flow speed. For the other microorgan models, the rotation speed of the microrobot pumps 100f and 100g is controlled to achieve a relatively high flow speed.

According to the present invention, a feedback controller configured to monitor the characteristics or bio-changes of a microorgan matches data about the intrinsic characteristics of the microorgan and a bio-change monitoring result according to administration of a drug or the like and transmits a feedback control signal for controlling the fluid flow.

Upon receiving the feedback control signal, the local magnetic field controller 410 (which is an element applying a local magnetic field for controlling driving of the microrobot pumps) applies a magnetic field 410m having a changed direction and intensity. Thereby, the rotation speed and direction of the microrobot pumps 100f and 100g are varied to adaptively reproduce the fluid flow.

The feedback controller adaptively implements change of the fluid speed by varying the rotation speed of the microrobot pumps 100f and 100g according to the result of monitoring of the state of the microorgan.

For example, when the heart rate of the cardiac organ model 200d is lowered, the rotation speed of the microrobot pumps 100f and 100g is controlled to be low. When the heart rate of the cardiac organ model 200d is increased, the rotation speed of the microrobot pumps 100f and 100g is controlled to be relatively high. Thereby, physiological effects such as changes in blood flow speed according to cardiac conditions in the actual body are simulated.

According to the present invention, the feedback controller detects a physiological effect such as a heartbeat through a separate imaging device or sensor and transmits a feedback control signal to the local magnetic field controller to change the rotation speed and direction of the microrobot pumps 100f and 100g. Accordingly, a function close to the actual animal and human models can be implemented in terms of an interaction due to an environmental change caused by the intrinsic characteristics of the microorgan, drug administration, or the like.

According to the embodiment of the present invention, the magnetic field 420m is applied to the entire area, or the magnetic field 410m is locally applied to the respective divided areas (an area where the microorgans are arranged and an area where the microrobot pumps are arranged).

Figure 3:
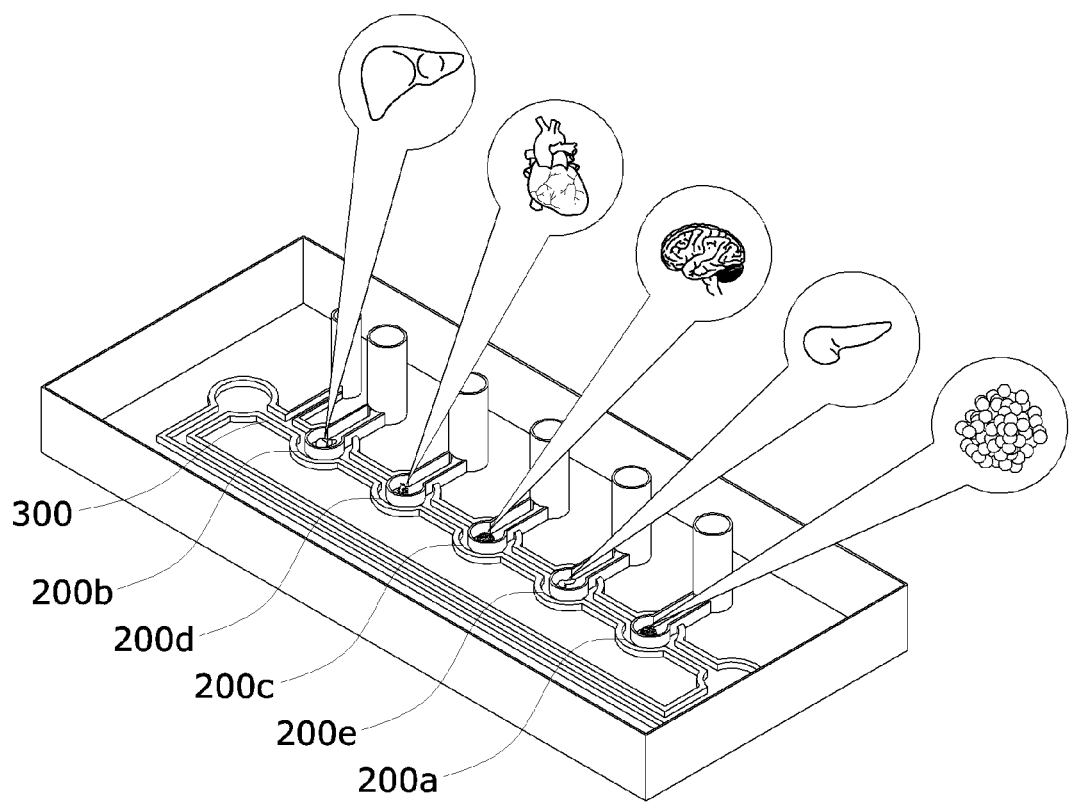
FIG. 3 is a perspective view illustrating the microrobot-based biometric system according to one exemplary embodiment of the present invention.
Figure 4:
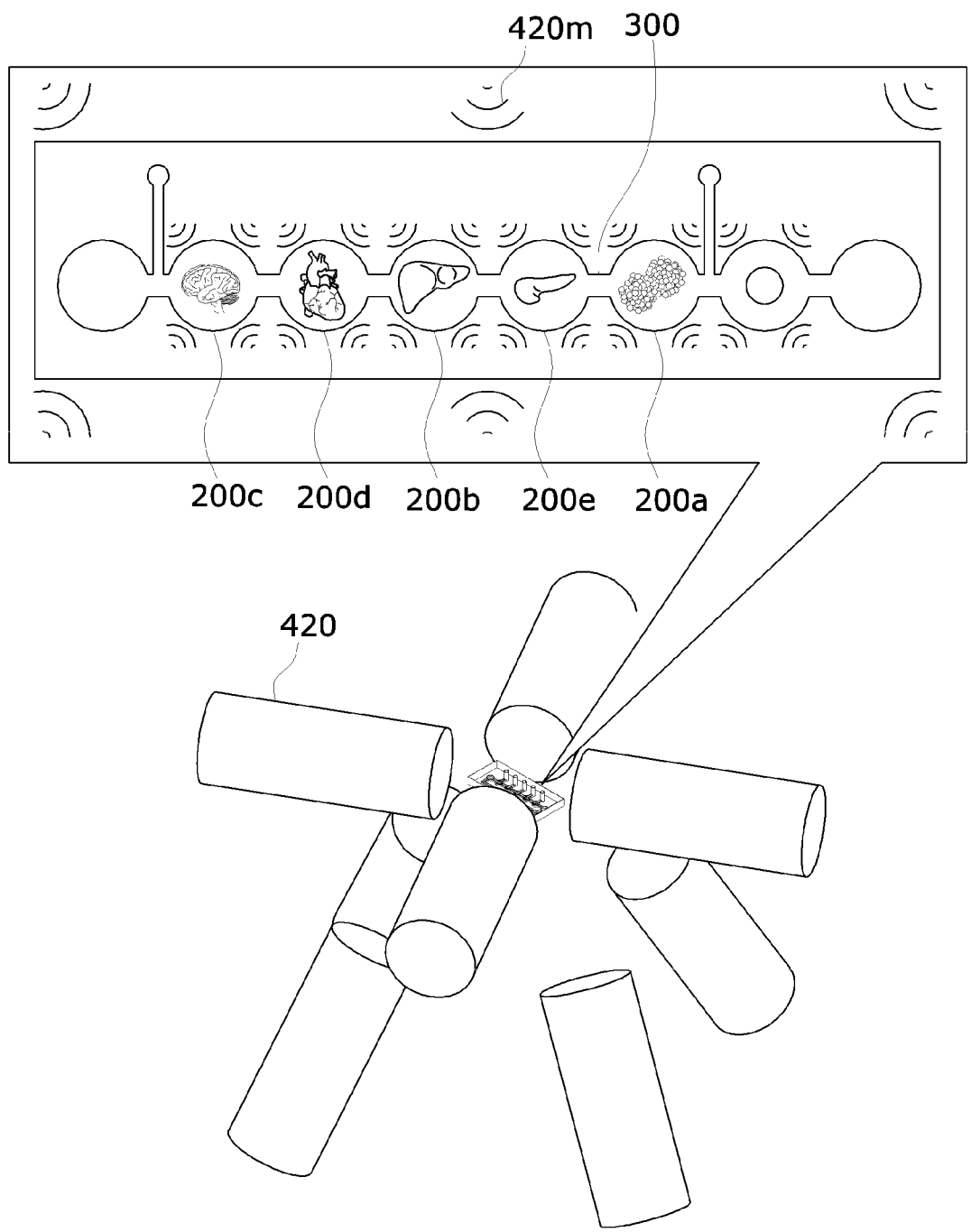
FIG. 4 is a view showing a global magnetic field controller and a local magnetic field controller according to one exemplary embodiment of the present invention.

Referring to FIGS. 3 and 4, the microrobots 100a and 100b configured to perform cell or drug delivery are introduced into the network 300 and transported by the magnetic field 420m applied by the global magnetic field controller 420. Upon reaching a target, the microrobots 100a and 100b are precisely controlled by the magnetic field 410m applied by the local magnetic field controller 410 to perform cell or drug delivery to an in vivo local portion to test a biological response and effect.

As described above, upon reaching the target, the microrobots 100a and 100b are caused by a preset magnetic field gradient or a rotating magnetic field to release the loaded cell or drug according to the shape thereof.

The local magnetic field controller 410 is arranged in the network connecting the microorgans 200 to each other or in the area of the microorgans.

Referring to FIG. 4, the local magnetic field controller 410 includes a plurality of micro-coils arranged in an area outside a chamber, in which the microorgan 200a is arranged, to apply a magnetic field toward the interior of the chamber. Each of the local magnetic field controllers 410 has an area for forming an independent magnetic field, and the global magnetic field controller 420 has a working space over the entire area of the biomimetic system.

The global magnetic field controller 420 and the local magnetic field controllers 410 apply a magnetic field to the corresponding areas by varying the direction and intensity of the magnetic field with respect to three axes (x, y, z), namely, roll, pitch, and yaw.

When the local magnetic field controllers 410 locally form individual magnetic fields, the local magnetic field controllers 410 precisely control the positions of the microrobots 100a and 100b transported through the network 300 in order to arrange the microrobots individually at a preset position of the microorgan 200a.

The magnetic field applied by the global magnetic field controller 420 described above is used to perform position control of the microrobots for movement in the network 300.

The global magnetic field controller 420 applies the magnetic field 420m to a target area through control of the relative positions or angles of the plurality of coils included therein.

The global magnetic field controller 420 precisely controls the positions of the plurality of microrobots at the same time to control the microrobots individually or collectively such that the microrobots are arranged at a preset position of the microorgan.

The local magnetic field controller 410 according to the embodiment of the present invention controls the microrobots such that the microrobots bypass the corresponding area depending on whether the microorgan in the area where the microrobots are arranged corresponds to the target or precisely controls the positions of the microrobots such that the microrobots face the microorgan in the corresponding area.

Hereinafter, in order to facilitate understanding of the invention by those skilled in the art, the present embodiment will be described on the assumption that a drug is released to the tumor 200a, which is a target, using the bio-scaffold type microrobot 100a.

Figure 5:
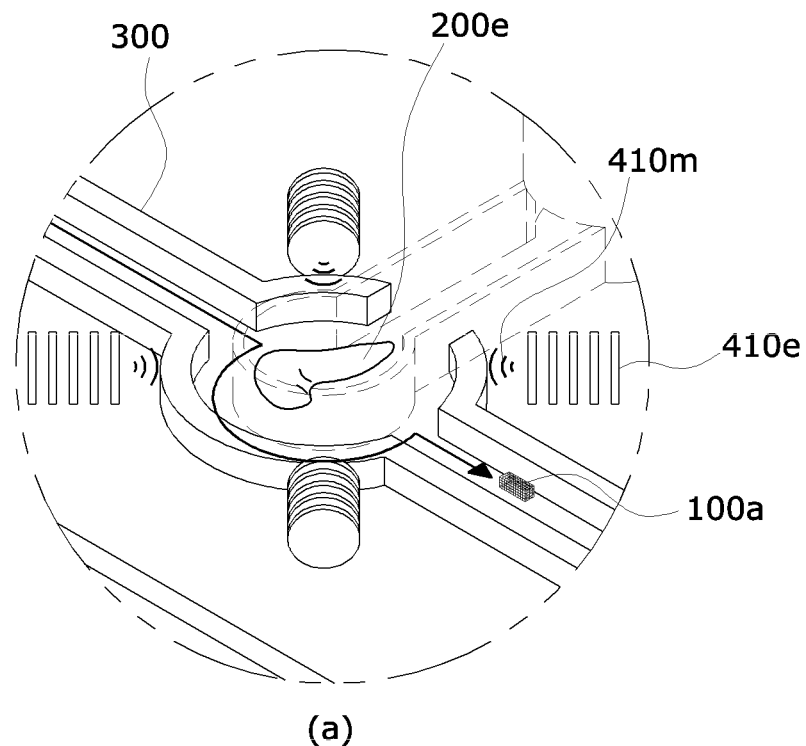
FIG. 5 is a view illustrating a microrobot precision control process of the local magnetic field controller according to one exemplary embodiment of the present invention.
Figure 5:
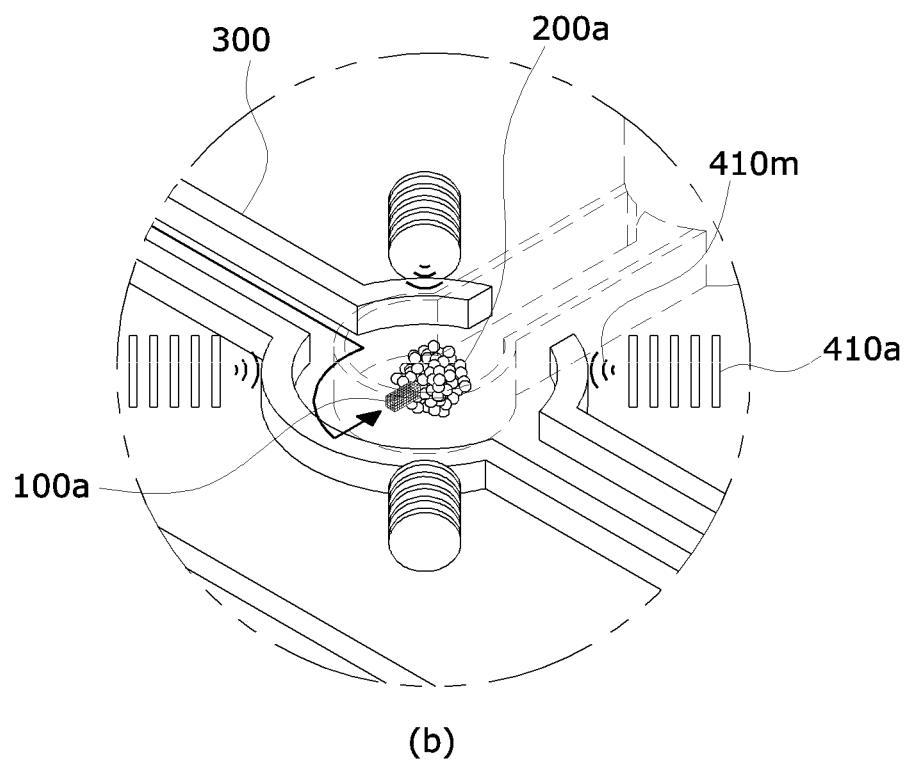

Referring to FIG. 5A, due to the system structure, the bio-scaffold type microrobot 100a, which is moved within the network 300 by magnetic field control, reaches a chamber area corresponding to the pancreas 200e before a path leading to the tumor 200a.

According to the assumption, the pancreas 200e does not correspond to the target, and accordingly, the bio-scaffold type microrobot 100a is caused to bypass the corresponding area by magnetic field control.

Here, the magnetic field control is performed in a manner in which the local magnetic field controller 410e arranged in the area of the pancreas 200e is turned off and the bio-scaffold type microrobot 100a is transported by the magnetic field applied thereto by the global magnetic field controller 420 described above.

The local magnetic field controller 410e arranged in the area of the pancreas 200e may apply a magnetic field not to cause the bio-scaffold type microrobot 100a to approach the pancreas 200e but to cause the bio-scaffold type microrobot 100a to bypass the corresponding area in the direction indicated by the arrow.

Referring to FIG. 5B, when the bio-scaffold type microrobot 100*a* enters the area of the tumor 200*a*, which is the target, the local magnetic field controller 410*a* arranged in the area performs precise magnetic field control on the bio-scaffold type microrobot 100*a* to control the position of the microrobot 100*a* toward the tumor 200*a* such that the drug is delivered.

Accordingly, when the bio-scaffold type microrobot 100*a* bypasses the chamber area, which is not the target, and enters the target area, the position thereof is precisely controlled by the magnetic field applied by the corresponding local magnetic field controller such that the microrobot releases the loaded drug towards the target.

The embodiments of the present invention have been described above. It will be understood by those skilled in the art that various changes in form and details can be made in the invention without departing from the spirit and scope of the invention. Therefore, the disclosed embodiments should be considered in an illustrative sense rather than a restrictive sense. The scope of the present invention is defined by the appended claims rather than by the foregoing description, and all differences within the scope of equivalents thereof should be construed as being included in the present invention.

The invention claimed is:

1. A microrobot-based biometric system comprising:
a plurality of chambers configured to contain microorgans, respectively, the microorgans comprising a target microorgan and a non-target microorgan;
a channel connecting the plurality of chambers that are disposed on a same surface as the channel;
at least one microrobot configured to move along the channel to perform target-directed delivery of a drug or cell; and
a magnetic field controller configured to control operation of the at least one microrobot, and comprising:
at least one global magnetic field controller configured to apply an external magnetic field to an entire area of the biometric system; and
a plurality of local magnetic field controllers configured to individually apply a local magnetic field to the plurality of chambers,
wherein when the at least one microrobot reaches an area of the non-target microorgan, a local magnetic field controller arranged in the area of the non-target microorgan, among the plurality of local magnetic field controllers, controls a plurality of micro-coils included in the local magnetic field controller to stop the plurality of micro-coils from generating the local magnetic field, and the least one global magnetic field controller controls a plurality of micro-coils included in the least one global magnetic field controller to continue to generate the external magnetic field to cause the at least one microrobot to bypass the area of the non-target microorgan,
the at least one microrobot comprises a first microrobot that comprises a cap configured to load the drug or cell and a plunger connected to the cap, and
when the first microrobot reaches the target microorgan, a local magnetic field controller arranged in an area of the target microorgan, among the plurality of local magnetic field controllers, applies a rotating magnetic field to the first microrobot to cause the plunger of the first microrobot to rotate and to cause the first microrobot to release the drug or cell from the cap.

2. The microrobot-based biometric system of claim 1, wherein the at least one microrobot comprises a second microrobot that comprises scaffolds and is configured to transport a three-dimensional culture cell or drug that is loaded in an internal space of the second microrobot.

3. The microrobot-based biometric system of claim 1, wherein the at least one microrobot comprises a plurality of microrobots,
wherein the global magnetic field controller simultaneously controls positions of the plurality of microrobots to collectively arrange the plurality of microrobots at preset positions of the microorgans.

4. The microrobot-based biometric system of claim 1, wherein the microrobot pump is fixed to a wall surface of the channel.

5. The microrobot-based biometric system of claim 1, wherein the microrobot pump is driven according to a length, height, angle, and degree of magnetization of a screw thread or blade thereof to vary a flow speed or direction of the fluid.

6. The microrobot-based biometric system of claim 1, further comprising a feedback controller configured to monitor characteristics or a bio-change of the microorgans,
wherein the microrobot pump varies the rotation speed or rotation direction thereof by the local magnetic field varied by a blood flow simulation control signal according to a monitoring result from the feedback controller.

* * * * *